US006970674B2

(12) United States Patent
Sato et al.

(10) Patent No.: US 6,970,674 B2
(45) Date of Patent: Nov. 29, 2005

(54) BELT TRANSPORTING DEVICE AND IMAGE FORMING APPARATUS USING THE SAME

(75) Inventors: Masahiro Sato, Kanagawa (JP); Atsuyuki Kitamura, Kanagawa (JP); Shinichi Kuramoto, Kanagawa (JP); Wataru Suzuki, Kanagawa (JP); Koichi Watanabe, Kanagawa (JP); Shuichi Nishide, Kanagawa (JP); Mituo Yamamoto, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 29 days.

(21) Appl. No.: 10/268,787

(22) Filed: Oct. 11, 2002

(65) Prior Publication Data

US 2003/0175056 A1 Sep. 18, 2003

(30) Foreign Application Priority Data

Mar. 15, 2002 (JP) .......................... P.2002-072943

(51) Int. Cl.[7] ....................... G03G 15/01; G03G 15/00; B65G 39/16; G16H 7/02

(52) U.S. Cl. ...................... 399/302; 399/162; 399/165; 198/806; 474/153; 474/167

(58) Field of Search ................................ 399/162, 165, 399/312, 313, 329, 302, 303, 164; 198/806, 198/807, 810.03, 837, 840; 347/154; 474/122, 474/101, 151, 190, 107, 123, 140, 153, 167, 474/901; 271/198

(56) References Cited

U.S. PATENT DOCUMENTS

| | | | | |
|---|---|---|---|---|
| 5,316,524 A * | 5/1994 | Wong et al. | ................ | 474/107 |
| 5,709,765 A * | 1/1998 | Herbert et al. | | |
| 5,943,540 A * | 8/1999 | Okamoto et al. | ........... | 399/302 |

FOREIGN PATENT DOCUMENTS

| | | | | |
|---|---|---|---|---|
| JP | 57060347 A * | 4/1982 | .......... | G03G 15/00 |
| JP | 57-76579 | 5/1982 | | |
| JP | 63057406 A * | 3/1988 | .......... | G03G 15/00 |
| JP | 6-27835 | 2/1994 | | |
| JP | 10186888 A * | 7/1998 | .......... | G03G 15/16 |
| JP | 10-282751 | 10/1998 | | |
| JP | 11-79457 | 3/1999 | | |
| JP | 11-161055 | 6/1999 | | |
| JP | 2001255778 A * | 9/2001 | .......... | G03G 21/00 |

* cited by examiner

*Primary Examiner*—Arthur T. Grimley
*Assistant Examiner*—Ryan Gleitz
(74) *Attorney, Agent, or Firm*—Morgan Lewis & Bockius LLP

(57) ABSTRACT

A belt transporting device for circulatingly transporting an endless belt, which is in use with an image forming apparatus, such as copying machine or a printer. The belt transporting device includes a plurality of tension rolls, an endless belt laid on the tension rolls, the endless belt having a belt-end edge part protruding from an end of one of the tension roll and a guide member provided in the vicinity of the endless belt. The guide member comes in contact with the belt-end edge part so as to bend the belt-end edge part in a tapering-off direction. The guide member regulates the shape of the belt-end edge part so that a rotary peripheral length of the belt-end edge part becomes smaller than that of an area where a rear side of the endless belt is in contact with the tension roll.

21 Claims, 6 Drawing Sheets

BELT TRANSPORTING DEVICE AND IMAGE FORMING APPARATUS USING THE SAME

BACKGROUND OF THE INVENTION

1. Field of the Invention

The present invention relates to a belt transporting device for circulatingly transporting an endless belt, which is in use with an image forming apparatus, such as copying machine or a printer. More particularly, the invention relates to a belt transporting device which is effective in preventing an inclination of the belt and an image forming apparatus using the same.

2. Background Art

Recently, in the image forming apparatus based on the electrophotography, for example, demands for size reduction, picture quality improvement, and cost reduction are increasing. To satisfy the demands, it is effective to employ the belt unit in the intermediate transfer body, sheet conveying body, fixing unit and the like.

In the intermediate transfer type image forming apparatus based on the electrophotography system, for example, which is already proposed, toner images of respective colors are successively formed on a photo receptor, those color toner images are primarily transferred onto the intermediate transfer body in a superimposed fashion, and those superimposed color images on the intermediate transfer body are simultaneously transferred onto a recording medium.

In this type of image forming apparatus, as known, the photo receptor takes a drum unit, and the intermediate transfer body takes the form of a belt unit (belt transporting device). The term "belt transporting device" means such a device that an endless belt is laid on a plurality of tension rolls, and the belt is circulatingly transported in a given direction.

In this type of belt transporting device, the belt does not linearly run, but runs while being biased to the axial direction of the roll, and hence there is the possibility that the belt inclines to its displaced direction, viz., a called inclined running of the belt occurs. Various factors causing this phenomenon are present: dimensional tolerances of structural components forming the belt transporting device, for example, parallelism of the rotary shafts of a plurality of tension rolls for supporting the belt in a stretching fashion, roll outside diameter variation, and tension unevenness of the belt owing to a variation of the periphery length of the belt.

A conventional belt-biasing preventing technique is present. In the technique, ribs are provided over the entire length of at least one end of the inner surface of the belt. The ribs are brought into engagement (contact) with (or fit to) grooves or the ends of the tension rolls to thereby regulate the belt inclination (see Japanese Patent Laid-Open No. 57-76579, for example).

Another technique for the belt-biasing prevention is that a flange of which the diameter is larger than the outside diameter of the tension roll is provided at least one end of the tension roll, and the belt, when runs, is restricted in motion at the end by the flange to forcibly be corrected in its running direction (Japanese Patent Laid-Open No. 06-27835).

The conventional techniques stated above have the following technical problems.

In the former or first conventional technique (based on the ribs), if the belt is biased in its running direction to one side of the belt and the ribs engage with the engaging parts (grooves, roll end or the like), and in this state, the biasing force continuously acts on the belt for a long time, stress repeatedly concentrates on the root of the rib (boundary part of the inner surface of the belt at which the rib is attached). The root of the rib will be cracked, and in an extreme case, the rib root is peeled off and the belt is seriously damaged.

The belt runs in a state that the ribs are constantly pressed against with the belt. In this state, non-uniformity of rib bonding accuracy will cause undulation and tilting in the running belt, so that the running belt will meander. When the belt meanders, the color toner images which are successively transferred onto the belt or the recording medium supported on the belt are shifted from the correct positions. As a result, a color picture finally formed on the recording medium suffers from image defects, such as color misregistration and hue variation.

The work of joining (bonding) of the ribs is troublesome, from the very beginning. Apart from this, to avoid the meandering of the running belt, it is essential to join (bond) the ribs to the belt with high precision. The rib bonding leads to cost increase, however, and in this respect, it is not a desirable measure.

In the second conventional technique (based on the flange), the end of the running belt is restricted by the flange to run following the belt end. When the running belt is biased and the biasing force continuously acts on the running belt in a state that the belt end is in contact with the flange, stress acts on the belt end and as a result, the belt is deformed to float up by the flange, viz., an undulation occurs in the belt. The undulation will crack the belt end, and in an extreme case, the belt is broken.

Even in a case where no undulation occurs, the flange frictionally slides on the side face of the belt end continuously, wear grows and hence, the durability performance is deteriorated.

An additional belt-biasing preventing technique is also proposed in which the roll is used in association with the belt surface in addition to the flange and ribs (Japanese Patent Laid-Open Nos. 10-282751 and 11-161055).

This technique is still unsatisfactory in solving the belt biasing problem since is complicated in construction and high in cost. While a chance of the belt cracking and damaging owing to the contact of the belt with the flange or ribs is lessened, indeed, the possibility that the belt is undulated by the end of the roll, and cracked and damaged is still present.

This possibility is great in particular where the biasing force is great. Further, certain accuracy is required for dealing with such a factor as parallelism.

A further belt-biasing preventing technique is proposed in which a tapered roll is disposed on the inner surface of the belt, and corrects the running belt biased outside from the end part of the tension roll (Japanese Patent Laid-Open No. 11-79457).

This technique also requires certain accuracy for the placement of the tapered roll, and is complicated in construction. A possibility that the undulation, cracking and damaging of the belt occurs in a gap part between the tension roll and the tapered roll is present. Accordingly, certain degree of accuracy is required for the belt-biasing causing factor, such as a parallelism of the roll, as in the previous techniques.

As described above, the conventional belt-biasing preventing techniques still have technical problems to be solved: at the contact part of the belt where it contacts with the regulating member, such as the flange or the ribs, the end part of the auxiliary roll, and the gap, the stress generated therein by the biasing force give rise to the undulation, meandering, cracking, damaging of the belt.

In the case additionally using the auxiliary roll, the construction is further complicated, and disadvantageous also in the light of cost.

SUMMARY OF THE INVENTION

It is an objective of the present invention to provide a belt transporting device in which no stress is generated when the biasing of the belt is regulated, and with an extremely simple construction, the belt biasing and damaging are prevented, and the secondary troubles of belt meandering and the like is effectively avoided.

According to a broad aspect of the invention, there is provided a belt transporting device for circulatingly transporting an endless belt 1 laid on a plurality of tension rolls 2 (e.g., 2a to 2d), wherein guide members 3 are provided near said endless belt 1, each said guide member 3 coming in contact with a belt-end edge part 4 protruded from one end of said tension roll 2, and bending said belt-end edge part 4 in a tapering-off direction (FIGS. 1(a) to 1(c)).

According to another broad aspect of the invention, there is provided a belt transporting device for circulatingly transporting an endless belt 1 laid on a plurality of tension rolls 2 (e.g., 2a to 2d), wherein guide members 3 are provided near the endless belt 1; the guide member 3 regulates the shape of a belt-end edge part 4 protruding from one end of the tension roll 2 so that a rotary peripheral length of the belt-end edge part is smaller than an area where a rear side of the endless belt is in contact with the tension roll 2 (FIGS. 1(a) to 1(c)).

In implementing the technical idea mentioned above, material of the endless belt may be material appropriately selected in accordance with the use of the belt transporting device.

The endless belt 1 may be a non-elastic belt as well as an elastic belt since it is considered that a bending regulation and a configuration regulation of the belt-end edge part 4 as defined above may be realized by using the non-elastic belt.

However, use of the elastic belt is preferable since the guiding by the guide members 3 is easy if the elastic belt is used.

In other words, the utilization of elasticity makes it easy to realize the bending and configuration of the belt-end edge part 4 as defined above. Even if a part of the endless belt 1 is elastically deformed, it is easy to retain a planarity in the remaining portion of the endless belt.

The belt-end edge part may always protrude from the tension roll or temporarily protrude therefrom with the meandering (biasing) of the endless belt 1.

In this sense, the endless belt 1 may be longer or shorter in the axial direction of the tension roll 2.

However, to securely regulate the biasing of the endless belt 1 in the running direction, it is preferable that the endless belt has a width larger than that of the tension roll, and the belt-end edge part is always protruded from the tension roll.

The embodiment always makes effective the belt biasing regulation by the belt-end edge part 4 to thereby ensure the regulation of the biasing of the endless belt 1.

Further, the guide members 3 may appropriately take any form if it satisfies the requirement that the guide members 3 is provided in the vicinity of the endless belt 1 abutting on the belt-end edge part 4 and bending the belt-end edge part 4 in a tapering-off direction.

The phrase "tapering-off direction" as used herein indicates a direction in which an end of the belt-end edge part is directed tapered toward the axial center of the tension roll 2.

In this case, the guide member 3 bends the belt-end edge part 4 in a predetermined direction, and generates in the belt-end edge part 4 a counter force F2 (directed toward the inner part of the endless belt 1 as viewed in the width direction of the belt) which is counter to a biasing force F1 of the endless belt 1, depending on a bending angle θ of the belt-end edge part 4

For this reason, the guide member 3 prevents the biasing action of the endless belt 1 in the running direction by increasing the ending angle θ.

The guide members 3 are preferably provided at both ends of the endless belt 1. A case where the biasing direction of the endless belt 1 is limited to a given direction, the guide member may be provided on one end of the endless belt 1.

When the operation of the guide members 3 is considered from another aspect, as shown in FIG. 1(c), for example, the guide member 3 is provided near the endless belt 1, and configures the belt-end edge part 4 so that a rotary peripheral length of the belt-end edge part 4 is shorter than that of the endless belt 1 being in contact with the tension rolls 2.

In this case, the guide member 3 regulates the configuration of the belt-end edge part 4 and generates in the belt-end edge part 4 a counter force F2 (directed toward the inner side of the endless belt 1 as viewed in the width direction of the belt) which is counter to a biasing force F1 of the endless belt 1, depending on a difference between those rotary peripheral lengths.

For this reason, the guide member 3 prevents the biasing action of the endless belt 1 in the running direction by increasing the rotary peripheral length difference.

The reason why the guide member 3 is employed follows.

In the belt transporting device which uses an elastic belt for the endless belt 1, when the endless belt 1 is biased to run off the tension roll 2 as shown in FIG. 2, the belt-end edge part 4 running off is released from its pressure by a tension caused by the tension roll 2, and inclines to the axial direction of the tension roll 2 by its elastic compression force.

At this time, the inclination causes the successively transported endless belt 1 to run in such a direction E as to wind and drag the belt to the center of the tension roll 2. When the winding/dragging force is equal to the biasing force, the endless belt 1 stably runs while not be biased.

A magnitude of the winding/dragging force which is counter to the biasing force is determined depending on an inclination angle and a length of the belt-end edge part (protruded part) 4.

More exactly, the inclination angle of the belt-end edge part varies depending on a tension of the endless belt 1. As the tension becomes higher, the inclination angle becomes larger. In this case, however, a rigidity of the belt transporting device must be increased disadvantageously.

In a situation that a tension of the endless belt 1 is relatively small (e.g., 5 kgf [5×9.8N or smaller), as shown in FIG. 3, the inclining of the belt-end edge part 4 is small and the winding/dragging force does not act.

One of effective ways to increase the inclination angle and stabilize the winding/dragging force is that the guide member 3 is disposed as stated above.

The guide member 3 may be disposed at any position if it is near the endless belt 1, and the bending and configuration of the belt-end edge part 4 as defined above are achieved. To more securely regulate the biasing of the endless belt 1, it is preferable that the guide member is disposed near one of the tension rolls.

This is based on the fact that the counter force F2 caused by the bending of the belt-end edge part 4 most effectively acts at the bending angle θ when the endless belt 1 passes the tension roll 2.

A preferable layout of the guide member 3 is that functional members which are brought into contact with and separated from the endless belt is not disposed at a part opposed to said tension roll associated with said guide member located nearby.

The functional member as used herein means a cleaning device, a transfer device or the like. Since those functional members constitute drive means for coming in contact with and separated from the endless belt 1, the constituent parts are disposed around the tension roll 2.

To effectively locate the guide member 3, it is preferable that the guide member 3 is disposed near the tension roll 2 which does not form the functional member, such as the cleaning device, transfer device or the like.

Another preferable layout of the guide member 3 is that the guide member 3 is disposed near the tension roll 2 having the largest winding angle at which the tension roll 2 comes in contact with the endless belt 1.

The guide member 3 is disposed near the tension roll having the largest winding length over which the tension roll comes in contact with the endless belt.

A further preferable layout of the guide member 3 is that the guide member 3 is disposed at a part opposed to a central part of a winding area of the endless belt 1 on the tension roll 2.

The reason why "a part opposed to a central part of a winding area of the endless belt 1 on the tension roll 2" is selected is that a pressure by the tension caused by the belt-end edge part 4 is low at this part, and hence this part allows the guide member to easily bend and configures this part the belt-end edge part by the guide member.

Exactly, at each of the entrance and exit of the belt 1 winding area of the tension roll 2, a bending force acts in such a direction as to taper off the belt-end edge part 4 (in the axial direction of the tension roll 2) under the pressure caused by the tension of the endless belt 1. At the central part of a winding area of the endless belt in the peripheral direction of the tension roll, the pressure caused by the tension of the endless belt 1 is small, and a quantity of bending to the axial direction of the belt-end edge part 4 is small. Therefore, if the guide member 3 is disposed corresponding to a central part of a winding area of the endless belt 1, the effect of increasing the bending angle θ of the belt-end edge part 4 is large, and hence the belt 1 biasing effect is large. In this sense, it is preferable to dispose the guide member so.

A preferable configuration of the guide member 3 is that a guide surface of the guide member at which the guide member comes in contact with said endless belt is arcuate with its center being substantially coaxial with the tension roll.

To bend the belt-end edge part 4 in the tapering-off direction at an area of the belt 1 winding part of the tension roll 2, which is as large as possible is effective for the winding and dragging of the endless belt 1 toward the inner part of the endless belt 1 as viewed in the width direction of the belt.

A preferable construction of the guide member 3 is that said guide member includes a slidable guide part which is slidable on said edge part of said endless belt.

This construction is preferable in that a stress of the guide member in connection with the endless belt 1 is reduced.

It should be understood that the invention is not limited to the belt transporting device, but may be implemented in the image forming apparatus using the belt transporting device, such as copying machine and printer.

In this case, as shown in FIG. 1(*a*), an image is formed on and held by an image forming/bearing body 8. The image is transferred from the image forming/bearing body 8 onto an intermediate transfer body or a recording medium put on a medium transporting body. The belt transporting device 9 is applied to the intermediate transfer body or he recording medium.

If the belt transporting device is applied to the image forming apparatus, particularly the color image forming apparatus, the color misregistration caused by the biasing of the belt in the belt transporting device is effectively avoided. In this respect, the application of the belt transporting device to the color image forming apparatus is preferable. However, the black/white image forming apparatus is not eliminated from those apparatus and others to which the present invention is applicable, as a matter of course.

BRIEF DESCRIPTION OF THE DRAWINGS

FIG. 1(*b*) is a sectional view, partly broken, when viewed in a direction B in FIG. 1(*a*).

FIG. 1(*c*) is an enlarged view showing a part C in FIG. 1(*b*).

FIG. 6(*b*) is a sectional view as seen in an arrow B in FIG. 6(*a*).

DETAILED DESCRIPTION OF THE PREFERRED EMBODIMENTS

The preferred embodiments of the present invention will be described in detail with reference to the accompanying drawings.

<Embodiment 1>

Figure 1:
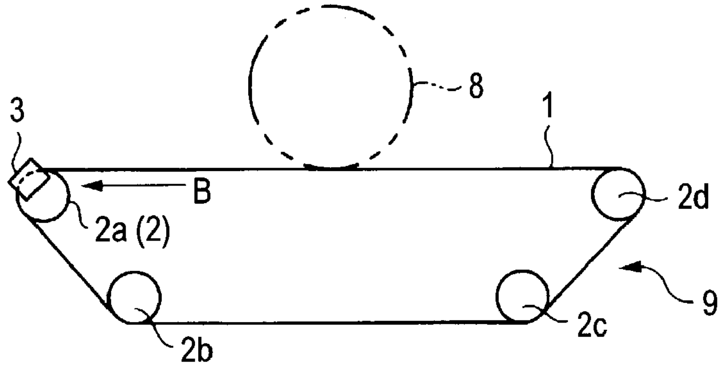
FIG. 1(*a*) is an explanatory diagram schematically showing a belt transporting device constructed according to the present invention, and an image forming apparatus using the same.
Figure 1:
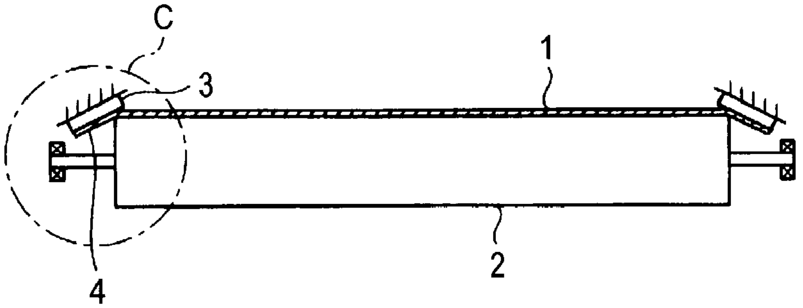
Figure 1:
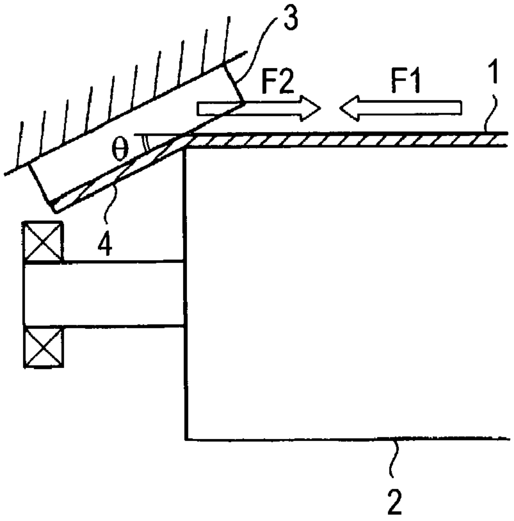
Figure 2:
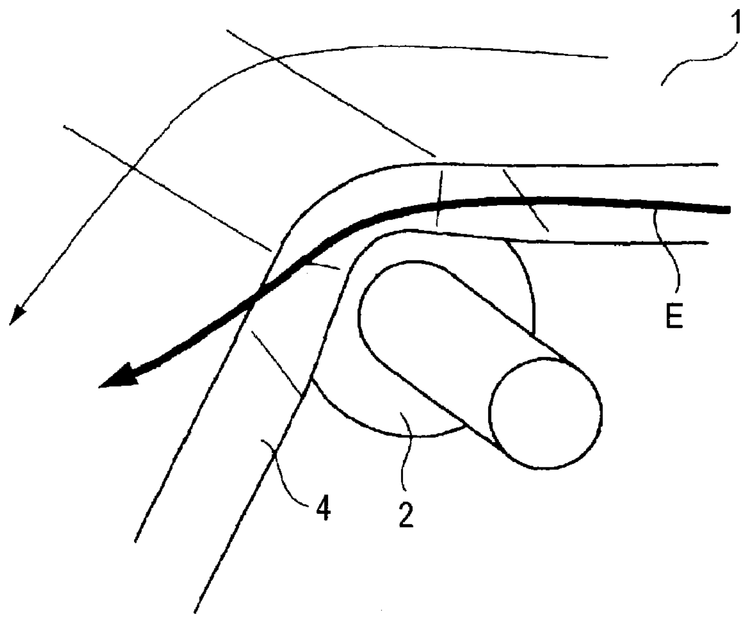
FIG. 2 is a diagram showing the running of the endless belt accompanied by natural winding/dragging caused by the belt-end edge part.
Figure 3:
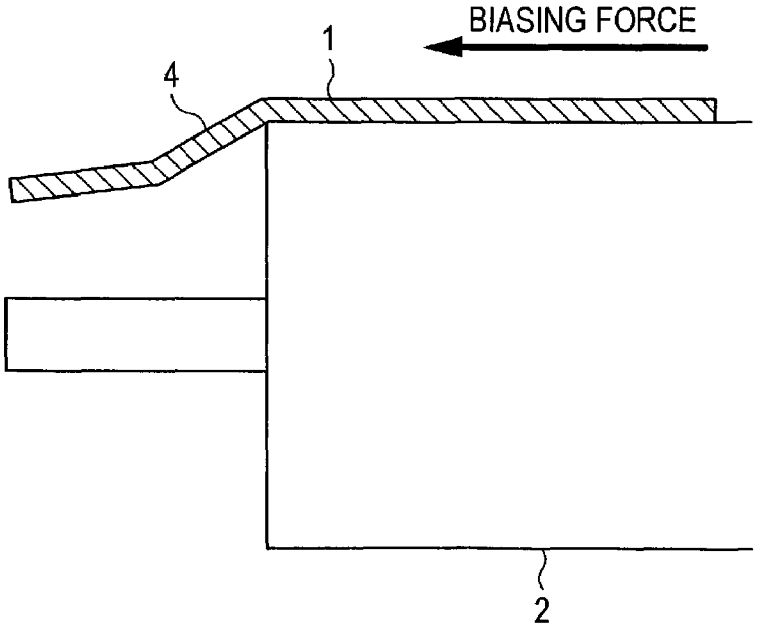
FIG. 3 is an explanatory diagram showing a problem of the natural winding/dragging caused by the belt-end edge part.
Figure 4:
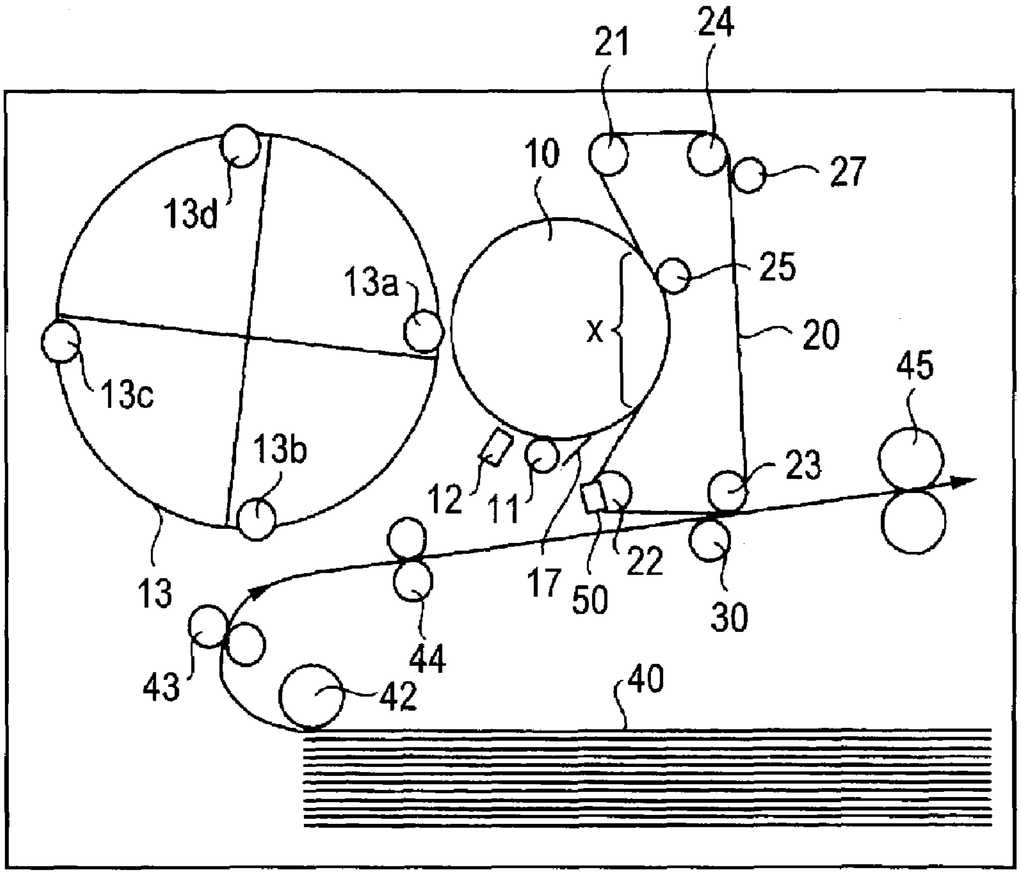
FIG. 4 is a diagram schematically showing an embodiment 1 of an image forming apparatus of the invention incorporating the present invention thereinto.

FIG. 4 is a diagram schematically showing an embodiment 1 of an image forming apparatus incorporating the present invention thereinto.

In the figure, the image forming apparatus includes a photo-receptor drum 10 and an intermediate transfer belt 20 which comes in contact with the photo-receptor drum 10 over a fixed area in a state that it extends along the shape of the photo-receptor drum 10, and receives a toner image from the photo-receptor drum 10.

In the instant embodiment, the photo-receptor drum 10 includes a photosensitive layer of which resistance reduces under illumination of light. Disposed around the photo-receptor drum 10 are a charger unit 11 for charging the photo-receptor drum 10, an exposure unit 12 for writing electrostatic latent images of respective colors (black, yellow, magenta, and cyan in the embodiment) onto the charged photo-receptor drum 10, a rotary developing unit 13 for developing the color latent images on the photo-receptor drum 10 into color toner images, the intermediate transfer belt 20, and a cleaning unit 17 for wiping out toner left on the photo-receptor drum 10.

The charger unit 11 may be a charging roll, and if necessary, such a charger as a corotron may be used for the charger unit.

The exposure unit 12 may be any unit if it is capable of writing images onto the photo-receptor drum 10 by light. In the embodiment, a print head using an LED may be used for the exposure unit. Other examples available for the exposure unit are a print head using an EL, and a scanner for scanning the photo-receptor drum surface with a laser beam from a polygon mirror.

The rotary developing unit 13 includes developing sub-units 13*a* to 13*d* containing respective color toners, which are rotatably supported. The rotary developing unit may take any form if it is capable of applying the color toner particles to the areas on the photo-receptor drum 10 which are reduced in potential as the result of exposure. There is no limit in the shape and particle diameter of toner used. Any kind of toner may be used if it is exactly put on the electrostatic latent image on the photo-receptor drum 10. The embodiment uses the rotary developing unit 13. Four developing units may be used instead.

The cleaning unit 17 may be any type of cleaning unit if it is capable of removing the residual toner on the photo-receptor drum 10. The cleaning unit of the blade cleaning type, for example, may be used for the cleaning unit. Where toner of a high transfer rate is used, the cleaning unit 17 may be omitted.

Polyimide or polycarbonate resin may be used for a material of the intermediate transfer belt 20. To effectively eliminate image defect, such as hollow character, it is necessary to reduce its contact surface pressure to the photo-receptor drum 10. In order to realize small walk and to omit a tension roll, it is preferable to use a rubber belt in which elastic rubber is used as its substrate (elastic layer).

In this case, to maintain the transfer performance, a volume resistivity of the elastic rubber substrate (elastic layer) of the intermediate transfer belt 20 must be selected to have a value necessary for retaining the transfer performance, for example, $10^6$ to $10^{12}\Omega\cdot$cm.

To remove dirt if it is attached to the surface of the intermediate transfer belt 20, the intermediate transfer belt 20 has preferably a multi-layer structure in which a release layer, e.g., a fluorine plastic layer, is layered on the surface of the elastic rubber substrate (elastic layer).

Young's modulus of the elastic layer is selected to be preferably within 15 to 80 MPa. The use of the elastic layer having such a physical property value provides a good transfer property.

Examples of the materials each having such a physical property value are urethane-based rubber (of the soft type: 16.9 MPa) and urethane-based rubber (of the hard type: 78.6 MPa), and chloroprene-based rubber (16.2 Mpa).

Conversely, examples of materials to be avoided in use are PET (1.47 GPa) and PC (1.96 GPa).

The width of the intermediate transfer belt 20 may be appropriately selected. In the embodiment, the width of it is selected to slightly exceed the axial length of the tension roll 22.

In the embodiment, the intermediate transfer belt 20, as shown in FIG. 4, is laid on four tension rolls 21 to 24, and is brought into contact with only a close contact area on and along the surface of the photo-receptor drum 10, which is located between the rotary developing unit 13 and the cleaning unit 17.

In the embodiment, the contact area (contact length x) where the intermediate transfer belt 20 comes in contact with the photo-receptor drum 10 is selected so as to satisfy a relation a+b+c+d<x where the contact lengths "x" of the tension rolls 21 to 24 to the intermediate transfer belt 20 are a, b, c and d (not shown).

The photo-receptor drum 10 and the intermediate transfer belt 20 may have drive sources, respectively. In the embodiment, however, the photo-receptor drum 10 is used as a drive source, and transmits its drive force to the intermediate transfer belt 20 via the contact area (contact length x), whereby the intermediate transfer belt 20 is rotated following the rotation of the photo-receptor drum 10.

Of the four tension rolls 21 to 24 of the intermediate transfer belt 20, the tension roll 21 located upstream of the transfer position serves as a drive roll, for example. The tension roll 22 located downstream of the transfer position serves as a follower roller, and regulates is contact area with the photo-receptor drum 10. In the embodiment, the winding angle of the intermediate transfer belt 20 on the tension rolls 21 and 22 is larger than that on the tension rolls 23 and 24. The tension roll 23 located downstream of it is a follower roller, and serves also as a back roll (earthed in the embodiment) for the secondary transferring operation. Further, the tension roll 24 serves also as a backup roll for a belt cleaning device 27 (the roll cleaning method is employed in the embodiment), for example. The size of the four tension rolls 21 to 24 may be appropriately selected in the embodiment.

The reason why the four tension rolls 21 to 24 are used for the intermediate transfer belt 20 in the embodiment follows.

To minimize the undulation of the surface of the intermediate transfer belt 20 and stabilize the movement of the intermediate transfer belt 20 in the axial direction from the photo-receptor drum 10 side, two tension rolls 21 and 22 must be located upstream and downstream of the photo-receptor drum 10 to determine a positional relation between the photo-receptor drum 10 and the intermediate transfer belt 20.

If the belt cleaning device 27 in contact with the outer periphery of the intermediate transfer belt 20 and a secondary transfer roll 30 to be described later are disposed at positions outside the tension rolls 21 to 24, a force to move the intermediate transfer belt 20, which is in contact with the inside surface of the intermediate transfer belt 20, in the axial direction is instable. This will lead to the meandering motion of the intermediate transfer belt 20.

To lessen or stabilize its effect, it is necessary to provide those devices (belt cleaning device 27 and secondary transfer roll 30) in association with the tension roll.

It is difficult to install those devices for one tension roll in the light of securing satisfactory space and performances of them. It is for this reason that the tension rolls 23 and 24 must be provided for the purpose of installing the belt cleaning device 27 and the secondary transfer roll 30.

Consequently, at least four tension rolls 21 to 24 are preferably used for the tension rolls on which the intermediate transfer belt 20 is wound.

In a case where as shown in FIG. 4, the photo-receptor drum 10 is brought into contact with the intermediate transfer belt 20, as a distance between the photo-receptor drum 10 and each of the tension rolls 21 and 22 located upstream and downstream of the photo-receptor drum 10 is longer, an action to correct the meandering of the intermediate transfer belt 20 on the photo-receptor drum 10 side is more stable.

To this end, in the embodiment, it is preferable to bring the photo-receptor drum 10 into contact with at a position at which the axis-to-axis distance between the tension rolls 21 and 22 is longest.

Figure 5:
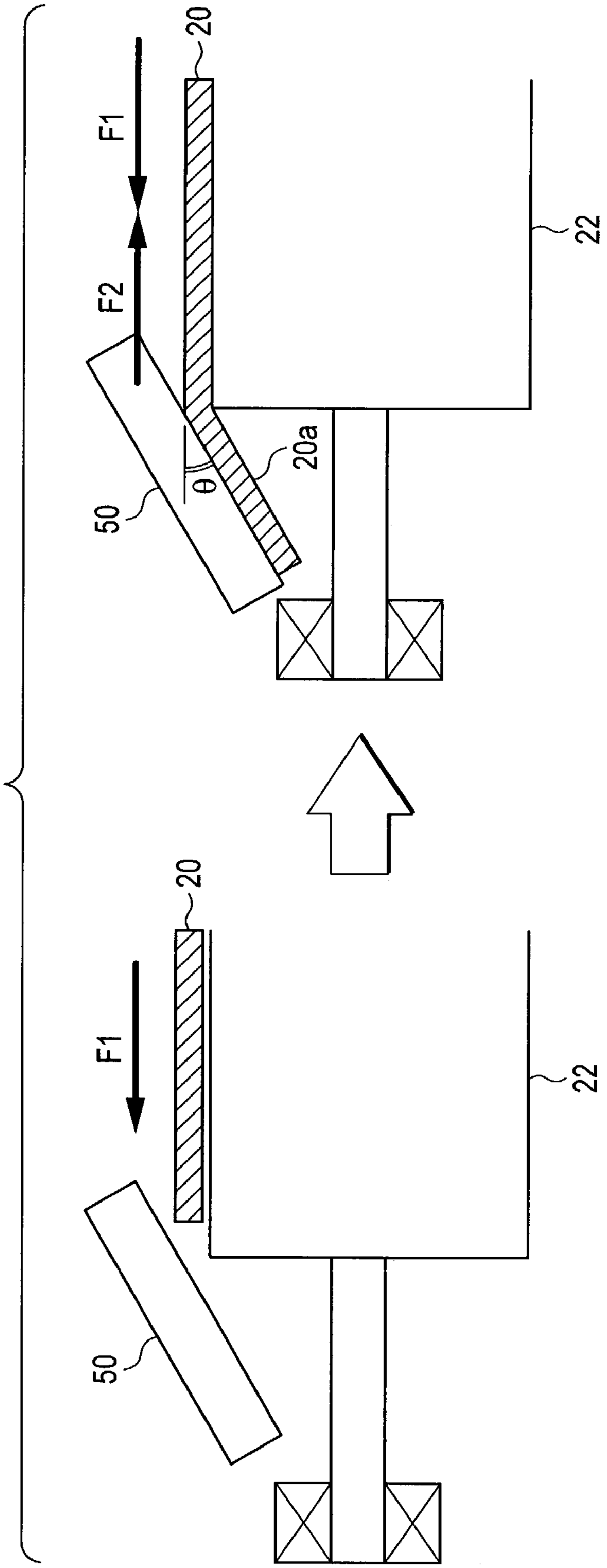
FIG. 5 is an explanatory diagram showing a belt transporting device used in the embodiment.

In particular, in the instant embodiment, a guide member 50 is fixedly provided near both ends of the tension roll 22 as shown in FIGS. 4 and 5.

The guide member 50 is made of POM (polyacetal) resin, for example, and shaped like a plate. When the intermediate transfer belt 20 is biased to run off the end of the tension roll 22, the run-off part of the intermediate transfer belt comes in contact with the surface of the belt-end edge part 20*a* and is forcibly bent in a tapering-off direction.

An inclination angle of the guide member 50, viz., a bending angle θ of he belt-end edge part 20*a*, imparts a force F2, which is counter to a biasing force F1, to the belt-end edge part 20*a*, and is selected to be such an angle (e.g., about 10° to 30°) as to negate the biasing of the intermediate transfer belt 20.

In the embodiment, to provide an easy sliding of the intermediate transfer belt 20, its contact surface with the belt-end edge part 20*a* is covered with a low friction coating layer made of Teflon (trademark).

In the embodiment, on the rear side of the intermediate transfer belt 20, a primary transfer roll 25 as a primary transfer member is disposed at a part of the contact area where the intermediate transfer belt 20 is in close contact with the photo-receptor drum 10.

At a part of the intermediate transfer belt 20, which is opposed to the tension roll 23, the secondary transfer roll 30 is located with the tension roll 23 as a secondary transfer member. For example, a given secondary transfer bias voltage is applied to the secondary transfer roll 30, and the tension roll 23 serving also as the backup roll is earthed.

A recording medium 40, such as a recording sheet, is stored in a sheet supply tray (not shown), and after it is fed to a feed roll 42, it is guided to a secondary transfer part by way of a transport roll 43 and a register roll 44, and transported to a fixing unit 45.

Operation of the image forming apparatus of the instant embodiment thus far described will be described.

In the embodiment, toner images of the respective colors are successively formed on the photo-receptor drum 10. Then, those toner images are successively transferred onto the intermediate transfer belt 20 at the contact area (primary transfer position), and then are simultaneously transferred onto a recording medium 40 at the secondary transfer position.

During such an image forming process, the photo-receptor drum 10 is in contact with the intermediate transfer belt 20 at a relatively broad contact area (contact length x). Further, those are elastically pressed one against the other with the aid of elastic rubber belt member. A tuck surface pressure between the photo-receptor drum 10 and the intermediate transfer belt 20 is not so high. Further, the toner images are tucked with the elastic rubber belt. The toner images on the photo-receptor drum 10 are primarily transferred onto the intermediate transfer belt 20.

In this case, the images transferred onto the intermediate transfer belt 20 are free from image defects, such as hollow characters, caused by the large tuck pressure, and those images are transferred at a high transfer rate. The color picture on the recording medium 40 is retained at extremely high quality.

In the instant embodiment, when parallelism errors among the tension rolls 21 to 24 or other factors generate a biasing force F1 and it acts on the intermediate transfer belt 20, the side end of the intermediate transfer belt 20 run off one end of the tension roll 22, for example, as shown in FIG. 5. The belt-end edge part 20*a* protruded from one end of the tension roll 22 is abutted on the guide member 50, and bent at a bending angle θ in a tapering-off direction.

In turn, a counter force F2, which is counter to the biasing force F1, acts on the belt-end edge part 20*a* abutted on the guide member 50. Thus, the biasing of the belt-end edge part 20*a* is restrained. The intermediate transfer belt 20 runs while being wound and dragged to the inner part of the intermediate transfer belt 20 when viewed in the width direction, and continues a stable run in a state that the biasing force F1 balances with the counter force F2.

Further, in the instant embodiment, after the intermediate transfer belt 20 and the belt unit including the tension rolls 21 to 24 are attached to the apparatus body, or when the belt unit is distorted at the time of installation, there is a chance that the parallelism among the tension rolls 21 to 24 of the belt unit is retained, but those tension rolls 21 to 24 are arranged in the same direction.

In such a case, if the tension rolls 21 to 24 are inclined, then the intermediate transfer belt 20 may be biased in a direction, not intended.

In this connection, it is noted that in the embodiment, a contact length "x" of the photo-receptor drum 10 over which it contacts with the outer periphery of the intermediate transfer belt 20 is selected to be larger than the sum of (a+b+c+d) of the contact lengths of the tension rolls 21 to 24, which are in contact with the inner side of the intermediate transfer belt 20. The intermediate transfer belt 20 may be moved in a direction as intended in a manner that a twist of the belt unit is predicted, and the photo-receptor drum 10 is inclined to a predetermined direction.

Also in the embodiment, only the photo-receptor drum 10 contains the drive source. Accordingly, a drive mechanism exclusively used for the intermediate transfer belt 20 may be omitted. Further, when comparing with the belt transporting device in which the photo-receptor drum and the intermediate transfer belt are provided with the drive sources, respectively, the peripheral speed difference (due to rotation error of the drive sources and error in the drive transmission system), which are essential for the belt transporting device, does not exist.

As a result, no slip occurs between the photo-receptor drum 10 and the intermediate transfer belt 20, good image transfer performance may be retained.

<Embodiment 2>

Figure 6:
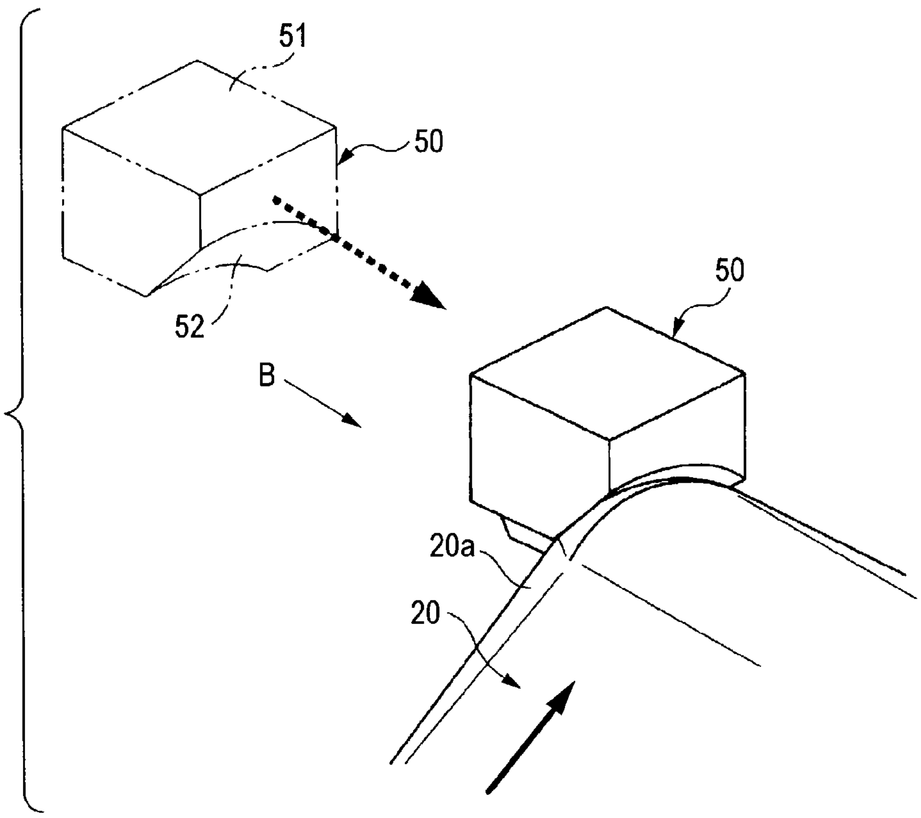
FIG. 6(*a*) is an explanatory diagram showing a key portion of a belt transporting device according to an embodiment 2 of the invention.
Figure 6:
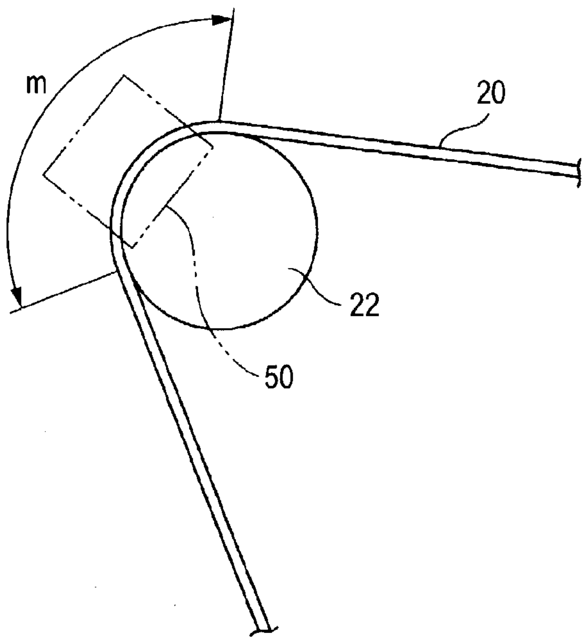

FIGS. 6(*a*) and 6(*b*) show a key portion of a belt transporting device (a belt unit having an intermediate transfer belt 20 assembled thereinto) in an embodiment 2.

In the figure, the belt transporting device, as in the embodiment 1, includes a guide member 50 located near a tension roll 22, but a construction of the guide member 50 is different from that in the embodiment 1.

The guide member 50 of the instant embodiment, as shown in FIGS. 6(*a*) and 6(*b*), includes a guide block 51 disposed at a part opposed to the central part of a winding area "m" of the tension roll 22. The guide block 51 includes an arcuate guide face 52 to be abutted on a belt-end edge part 20*a*.

Attention is paid to the intermediate transfer belt 20 passing the tension roll 22 in the instant embodiment. At each of the entrance and exit of the belt 1 winding area "m" of the tension roll 22, a pressure by the tension caused by the belt-end edge part 20*a* is large, and the belt-end edge part 20*a* is greatly bent in a tapering-off direction. At the central part of the belt winding area "m" of the tension roll 22, the pressure by a tension of the belt-end edge part 20*a* is small. Accordingly, the belt-end edge part 20*a* is easy to be bent by the guide member 50. As a result, the guiding effect by the guide member 50 is enhanced correspondingly.

The bending effect by the guide member 50 is gained over a broad range by the shape of the guide face 52. Accordingly, the guiding effect by the guide member 50 is further enhanced.

<Embodiment 3>

Figure 7:
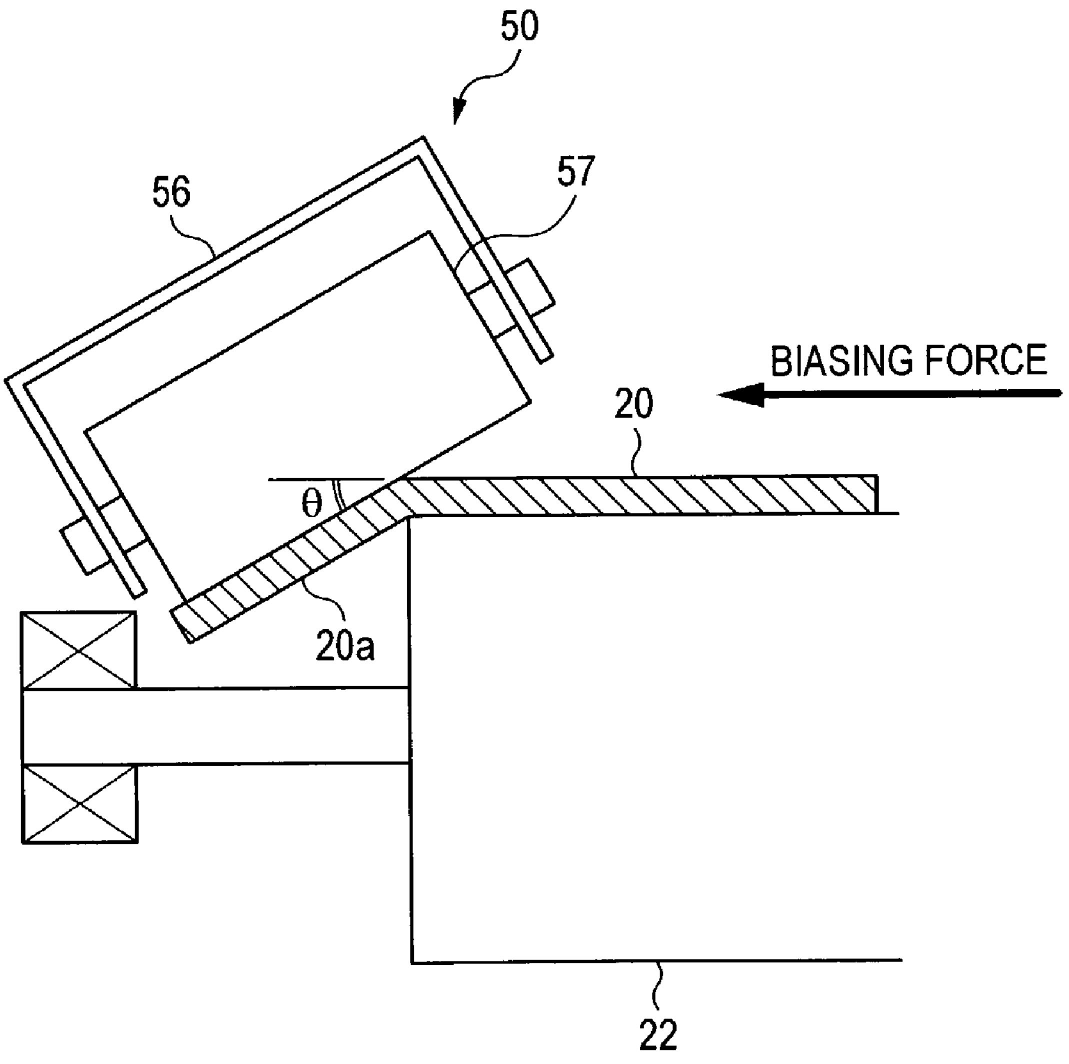
FIG. 7 shows a key portion of a belt transporting device in an embodiment 3 of the invention.

FIG. 7 shows a key portion of a belt transporting device (a belt unit having an intermediate transfer belt 20 assembled thereinto) in an embodiment 3.

In the figure, the belt transporting device, as in the embodiments 1 and 2, includes a guide member 50 located near a tension roll 22, but a construction of the guide member 50 is different from that in the embodiments 1 and 2.

The guide member 50 of the instant embodiment rotatably supports a guide roll 57 on a bracket 56. A belt-end edge part 20*a* protruded from one end of the tension roll 22 is brought into sliding contact with the rotational periphery surface of the guide roll 57 to regulate the bending.

In the embodiment, sliding resistance between the guide member 50 and the belt-end edge part 20*a* is extremely small in value. The running of the intermediate transfer belt 20 is not impeded by friction resistance associated with the guide member 50.

As seen from the foregoing description, in the invention, the guide member is provided near the endless belt, and the belt-end edge part protruded from one end of the tension roll is abutted on the guide member and bent in a tapering-off direction. Therefore, by the bending regulation by the belt-end edge part, a force counter to a biasing force may be imparted to the belt-end edge part.

Accordingly, no stress is generated when the biasing of the belt is regulated. With a simple construction, the belt biasing and damaging are prevented, and the secondary troubles of belt meandering and the like are effectively avoided.

Also in an image forming apparatus using such a belt transporting device, the belt biasing and damaging are prevented, and the secondary troubles of belt meandering and the like are effectively avoided. Therefore, the belt transporting operation may be stabilized considerably, and its image transfer quantity to the belt is retained at good condition correspondingly.

What is claimed is:

1. A belt transporting device comprising:

a plurality of tension rolls;

an endless belt laid between at least two of the plurality of tension rolls, the endless belt having a belt-end edge part protruding from an end of one of the plurality of tension rolls; and a guide member provided at the belt-end edge part protruding from the end of one of the plurality of tension rolls, wherein the guide member comes in contact with the belt-end edge part so as to bend the belt-end edge part in a direction in which an end of the belt-edge part is directed tapered toward an axial center of the one of the plurality of tension rolls.

2. The belt transporting device according to claim 1, wherein the endless belt is an elastic belt.

3. The belt transporting device according to claim 1, wherein the endless belt has a width larger than that of the one of the tension rolls so that the belt-end edge part protruded from the one of the tension rolls in an ordinary state.

4. The belt transporting device according to claim 1, further comprising a functional member to bring into contact with and separate from the endless belt; wherein the functional member is disposed at a part opposing to at least any one of the tension rolls except the one which is associated with the guide member.

5. The belt transporting device according to claim 1, wherein at least one of the tension rolls has the largest winding angle.

6. The belt transporting device according to claim 1, wherein at least one of the tension rolls has the largest winding length.

7. The belt transporting device according to claim 1, wherein the guide member includes a guide surface being in contact with the endless belt, and the guide surface forms an arc having a center being substantially coaxial with the tension roll.

8. The belt transporting device according to claim 1, wherein the guide member includes a slidable guide part being slidably in contact with the belt-end edge part.

9. The belt transporting device comprising:

a plurality of tension rolls;

an endless belt laid between at least two of the plurality of tension rolls, the endless belt having a belt-end edge part protruding from an end of one of the plurality of tension rolls; and a guide member provided in the vicinity of the endless belt, disposed in the vicinity of the one of the tension rolls, wherein the guide member comes in contact with the belt-end edge part so as to bend the belt-end part in a direction in which an end of the belt-edge part is directed tapered toward an axial center of the one of the plurality of tension rolls, and is disposed at a part opposing to a center part of a belt winding area of the one of the tension rolls in a peripheral direction of the tension roll.

10. A belt transporting device comprising:

a plurality of tension rolls;

an endless belt laid on the tension rolls, the endless belt having a belt-end edge part protruding from an end of one of the tension rolls; and a guide member provided in the vicinity of the endless belt;

wherein the guide member regulates the shape of the belt-end edge part so that a rotary peripheral length of the belt-end edge part becomes smaller than that of an area where a rear side of the endless belt is in contact with the tension roll.

11. The belt transporting device according to claim 10, wherein the endless belt is an elastic belt.

12. The belt transporting device according to claim 10, wherein the endless belt has a width larger than that of the one of the tension rolls so that the belt-end edge part protruded from the one of the tension rolls in an ordinary state.

13. The belt transporting device according to claim 10, wherein the guide member is disposed in the vicinity of the one of the tension rolls.

14. The belt transporting device according to claim 13, further comprising a functional member to bring into contact with and separate from the endless belt, wherein the functional member is disposed at a part opposing to at least any one of the tension rolls except the one which is associated with the guide member.

15. The belt transporting device according to claim 13, wherein the guide member is disposed in the vicinity of one of the tension rolls which has the largest winding angle.

16. The belt transporting device according to claim 13, wherein the guide member is disposed in the vicinity of one of the tension rolls which has the largest winding length.

17. The belt transporting device according to claim 13, wherein the guide member is disposed at a part opposing to a central part of a belt winding area of the one of the tension rolls in a peripheral direction of the tension roll.

18. The belt transporting device according to claim 13, wherein the guide member includes a guide surface being in contact with the endless belt and the guide surface forms an arc having a center being substantially coaxial with the tension roll.

19. The belt transporting device according to claim 10, wherein the guide member includes a slidable guide part being slidably in contact with the belt-end edge part.

20. An image forming apparatus comprising a belt transporting device, wherein the image forming apparatus comprises:

a plurality of tension rolls;

an endless belt laid on the tension rolls, the endless belt having a belt-end edge part protruding from an end of one of the plurality of tension rolls;

a guide member provided at the belt-end edge part protruding from the end of one of the plurality of tension rolls; and the guide member comes in contact with the belt-end edge part so as to bend the belt-end edge part in a direction in which an end of the belt-edge part is directed tapered toward an axial center of the one of the plurality of tension rolls.

21. An image forming apparatus comprising a belt transporting device, wherein the image forming apparatus comprises:

a plurality of tension rolls, an endless belt laid on the tension rolls, the endless belt having a belt-end edge part protruding from an end of one of the tension rolls;

a guide member provided in the vicinity of the endless belt; and the guide member regulates the shape of the belt-end edge part so that a rotary peripheral length of the belt-end edge part becomes smaller than that of an area where a rear side of the endless belt is in contact with the tension roll.

* * * * *